United States Patent [19]

Raffa et al.

[11] Patent Number: 5,468,744
[45] Date of Patent: Nov. 21, 1995

[54] COMPOSITION COMPRISING A TRAMADOL MATERIAL AND ANY OF CODEINE, OXYCODONE OR HYDROCODONE AND THEIR USE

[75] Inventors: Robert B. Raffa, Norristown; Jeffrey L. Vaught, Perkasie, both of Pa.

[73] Assignee: McNeilab, Inc., Spring House, Pa.

[21] Appl. No.: 268,382

[22] Filed: Jun. 30, 1994

Related U.S. Application Data

[63] Continuation of Ser. No. 976,728, Nov. 16, 1992, abandoned, which is a continuation of Ser. No. 755,923, Sep. 6, 1991, abandoned.

[51] Int. Cl.$^6$ ...................... A61K 31/485; A61K 31/135
[52] U.S. Cl. ............................................. 514/282; 514/646
[58] Field of Search ...................... 514/282, 646

[56] References Cited

U.S. PATENT DOCUMENTS 3,652,589   3/2872   Flick et al. .............................. 548/578

Primary Examiner—Raymond Henley, III
Assistant Examiner—William R. A. Jarvis
Attorney, Agent, or Firm—Ralph R. Palo

[57] ABSTRACT

This invention relates to compositions comprising a tramadol material selected from the group consisting of tramadol, its stereoisomers and its pharmaceutically acceptable salts and either codeine or oxycodone, and their use in treating pain. When the components, i.e., tramadol materials and either of codeine or oxycodone, of the composition are within certain ratios of pharmacological effects of the compositions are superaddditive (synergistic).

12 Claims, 2 Drawing Sheets

COMPOSITION COMPRISING A TRAMADOL MATERIAL AND ANY OF CODEINE, OXYCODONE OR HYDROCODONE AND THEIR USE

This is a continuation of application Ser. No. 07/976,728, filed Nov. 16, 1992, now abandoned which is a continuation of application Ser. No. 07/755,923, filed Sep. 6, 1991, now abandoned.

CROSS REFERENCE

This case is related to, but does not derive benefit under 35 U.S.C. 120 from application Ser. Nos. 07/974,863 and 07/974,865.

BACKGROUND OF THE INVENTION

U.S. Pat. No. 3,652,589 discloses a class of analgesic cycloalkanol-substituted phenol esters having a basic amine group in the cycloalkyl ring. The compound (1RS, 2RS) trans-2-[(dimethylamino)-methyl]-1-(3-methoxyphenyl)cyclohexanol, commonly known as tramadol, is specifically disclosed therein. A series of articles pertaining to the pharmacology, toxicology and clinical studies of tramadol are found in *Arzneim, Forsch (Drug Res.)*, 28(1), 114 (1978). Driessen et al., *Arch. Pharmacol.*, 341, R104 (1990) disclose that tramadol produces its analgesic effect through a mechanism that is neither fully opioid-like nor non-opioid-like. The *Abstracts of the VI th World Congress on Pain*, Apr. 1–6 (1990) discloses that tramadol hydrochloride is an orally active pure agonist opioid analgesic. However, clinical experience indicates that tramadol lacks many of the typical-side effects of opioid agonists, e.g., respiratory depression (W. Vogel et al., *Arzneim, Forsch, (Drug Res.)*, 28(1), 183 (1978)), constipation (I. Arend et al., *Arzneim, Forsch, (Drug Res.)*, 28(1), 199 (1978)), tolerance (L. Flohe et al., *Arzneim, Forsch, (Drug Res.)*, 28(1), 213 (1978)), and abuse liability (T. Yanagita, *Arzneim, Forsch. (Drug Res.)*, 28(1), 158 (1978)). When given at a dose of 50 mg by rapid i.v. injection, tramadol may however, produce certain side effects unique to tramadol including hot flushes and sweating. Despite theses side effects, tramadol's combination of non-opioid and opioid activity makes tramadol a very unique drug. Tramadol is currently being marketed by Grunenthal GMBH in Germany as an analgesic.

Opioids have for many years been used as analgesics to treat severe pain. However, they produce undesirable side effects which place limitations on their use. The side effect problems are well documented in the literature. See, Jaffe, J. in "Goodman and Gilman's The Pharmacological Basis of Therapeutics", 8th edition; Gilman et al.; Peragamon Press, New York, 1990; Chapter 22, pages 522–573, wherein it is disclosed that morphine and its congeners, e.g., codeine, hydrocodone and oxycodone, are opioid agonist analgesics that exhibit side effects such as respiratory depression, constipation, tolerance and abuse liability.

To reduce the side effect problems, opioids have been combined with other non-opioid analgesic agents so as to reduce the amount of opioid needed to produce equivalent analgesia. The reduced amount of opioid generally reduces the number and degree of the side effects. It has been claimed that some of these combination products also have the advantage of producing a synergistic analgesia effect. For example, A. Takemori *Annals New York Acad. Sci.*, 281, 262 (1976) discloses that compositions including combinations of opioid analgesics with drugs other than analgesics exhibit a variety of effects, i.e., subadditive (antagonistic), additive or superadditive. R. Taber et al., *J. Pharm. Expt. Thera.*, 169(1), 29 (1969) disclose that the combination of morphine and methadone, another opioid analgesic, exhibited only an additive effect. U.S. Pat. No. 4,571,400 discloses that the combination of dihydrocodeine, another opioid analgesic, and ibuprofen, a non-opioid analgesic, provides superadditive effects when the components are within certain ratios. A. Pircio et al., *Arch. Int. Pharmacodyn.*, 235, 116 (1978) report superadditive analgesia with a 1:125 mixture of butorphanol, another opioid analgesic, and acetaminophen (APAP), a non-opioid analgesic, whereas a 1:10 mixture did not show any statistically-significant superadditive analgesia.

However, the prior art, does not suggest or disclose that tramadol, an "atypical" opioid analgesic, can or should be combined with another analgesic, particularly an opioid analgesic, to lessen the side effects of each; or to yield a composition that exhibits superadditive analgesia.

SUMMARY OF THE INVENTION

It has now been found that a tramadol material which includes various forms of tramadol as defined hereinafter can be combined with certain opioids, codeine, oxycodone and hydrocodone, to produce an analgesic effect. Each of these opioids is a member of the class of opoids having the same core structure; i.e., each one has a 3-methoxy substituent on the aromatic moiety. The combination employs lesser amounts of both the tramadol material and the opioid than would be necessary to produce the same amount of analgesia if either was used alone. By using lesser amounts of both drugs the side effects associated with each are reduced in number and degree. Surprisingly, the compositions comprising a tramadol material and any of codeine, oxycodone or hydrocodone have been found to exhibit synergistic analgesic effects when combined in certain ratios. The compositions according to this invention may also be useful in treating tussive conditions and diarrhea.

BRIEF DESCRIPTION OF THE FIGURES

This invention may be more readily understood by reference to the following figures in which.

DETAILED DESCRIPTION OF THE INVENTION

Figure 1:
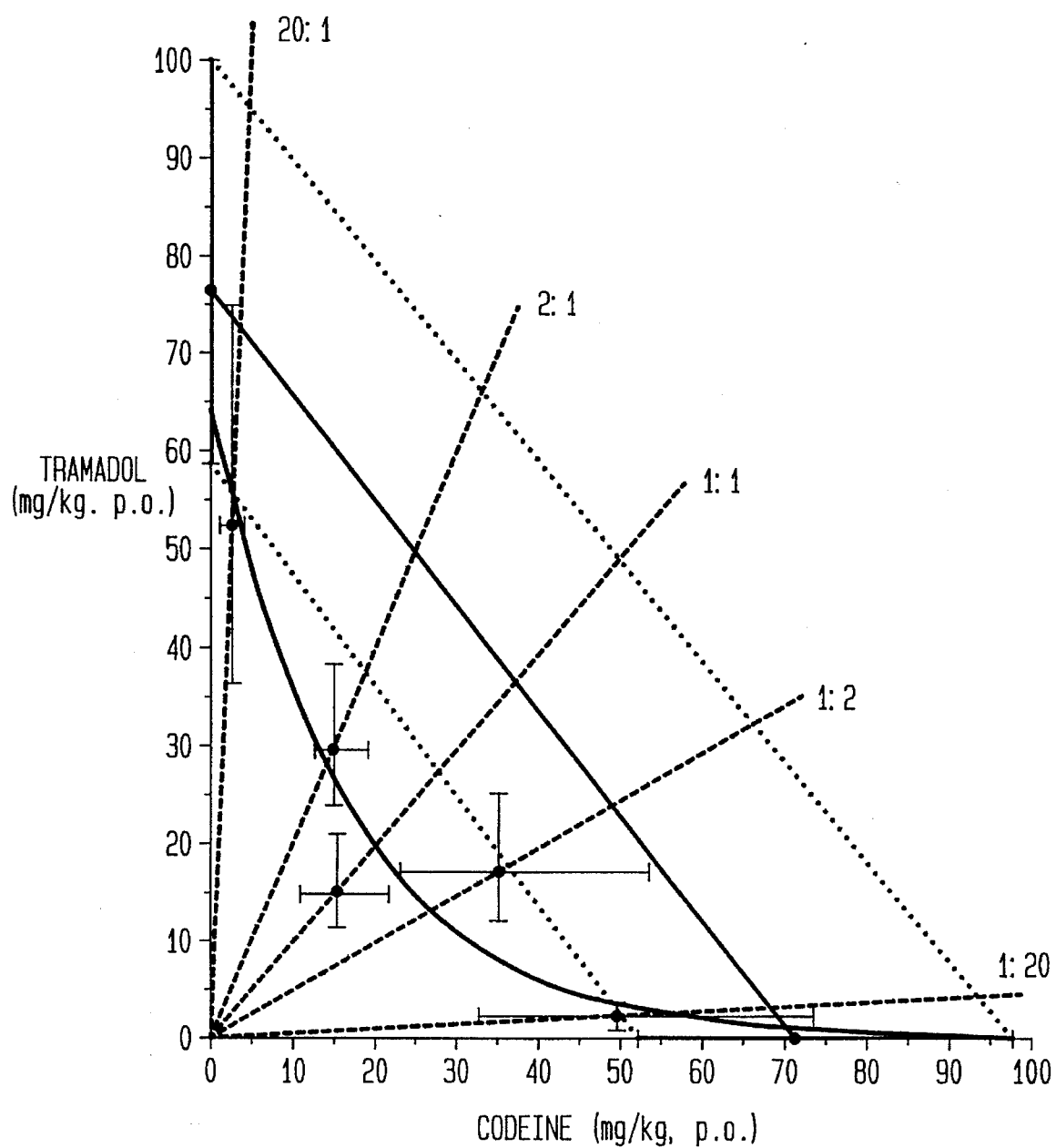
FIG. 1 is an isobologram showing the analgesic effect of tramadol hydrochloride and codeine phosphate compositions on tail-flick latency in mice.

The present invention is directed to compositions comprising a tramadol material and any one of codeine, oxycodone or hydrocodone and mixtures thereof.

The tramadol material according to the present invention is any one of (1R, 2R or 1S, 2S)-(dimethylaminomethyl)-1-(3-methoxyphenyl)-cyclohexanol (tramadol), its N-oxide derivative ("tramadol N-oxide"), and its O-desmethylated derivative ("O-desmethyl tramadol") or mixtures thereof. It also includes the individual stereoisomers, mixtures of stereoisomers including the racemates, pharmaceutically acceptable salts of the amines, such as the hydrochloride salt, solvates and polymorphs thereof. Tramadol is commercially available from Grunenthal or may be made by the process described in U.S. Pat. No. 3,652,589, which is herein incorporated by reference.

Tramadol N-oxide is prepared by treating tramadol as a free base with an oxidizing agent, e.g., hydrogen peroxide (30%), in an organic solvent, e.g., methanol or isopropanol, with, but preferably, without heating. See, "Reagents For Organic Synthesis", 1, 471, Fieser & Fieser eds., Wiley N.Y; (1987) and B. Kelentey et al., *Arzneim, Forsch.,* 7, 594 (1957). With heating, the reaction takes about 1 hour, whereas without heating the reaction takes about 3 days. Following the oxidation, the mixture is treated with an agent, e.g. $PtO_2$ or preferably Pt/C, for about a day, to destroy the excess hydrogen peroxide. The mixture is filtered, followed by the evaporation of the filtrate and then the residue is recrystallized from an organic solvent mixture, e.g., methylene chloride/ethyl acetate.

O-Desmethyl tramadol is prepared by treating tramadol as a free base under O-desmethylating reaction conditions, e.g., reacting it with a strong base such as NaH or KH, thiophenol and diethylene glycol (DEG) with heating to reflux. See, Wildes et al., *J. Org. Chem,,* 36, 721 (1971). The reaction takes about an hour, followed by the cooling and then quenching of the reaction mixture in water. The quenched mixture is then acidified, extracted with an organic solvent such as ethyl ether, basified and then reextracted with a halogenated organic solvent such as methylene chloride. The extract is then dried and the solvent is evaporated to yield the O-desmethylated product, which may then be short-path distilled, converted to its corresponding salt, e.g., treated with an acidic (HCl/ethanol) solution, and recrystallized from an organic solvent mixture, e.g., ethanol/ethyl ether.

Codeine, oxycodone and hydrocodone include their basic forms and pharmaceutically acceptable salts, such as phosphate, sulfate, hydrochloride and bitartrate, thereof. The preparation of each of codeine, oxycodone and hydrocodone is disclosed, respectively by Goto et al., *Proc. Japan Acad.,* 30, 769 (1954), Freund et al., *J. Prakt, Chem.,* 94, 135 (1916) and U.S. Pat. No. 2,715,626.

The tramadol material and the opioid material are generally present in a weight ratio of tramadol material to opioid material of from about 200:1 to 1:20. This ratio varies within the disclosed range depending upon the particular components of the composition. Certain ratios within this range will result in a composition which exhibits synergistic analgesic effects. For example, in a composition comprising tramadol and codeine the ratio of the components is from about 20:1 to 1:20, preferably from about 2:1 to 1:2, and, more preferably, from about 2:1 to 1:1. In a composition comprising tramadol and oxycodone, the ratio of the components is from about 200:1 to 1:1; more preferably from about 20:1 to about 2:1.

Pharmaceutical compositions comprising the tramadol material and any of codeine, oxycodone or hydrocodone as the active ingredients in intimate admixture with a pharmaceutical carrier can be prepared according to conventional pharmaceutical compounding techniques. The carrier may take a wide variety of forms depending on the form of preparation desired for administration, e.g., intravenous, oral or parenteral. The composition may also be administered by means of an aerosol. In preparing the compositions in oral dosage form, any of the usual pharmaceutical media may be employed. For example, in the case of oral liquid preparations (such as suspensions, elixirs and solution), water, glycols, oils, alcohols, flavoring agents, preservatives, coloring agents and the like may be used. In the case of oral solid preparations (such as, for example, powders, capsules and tablets), carriers such as starches, sugars, diluents, granulating agents, lubricants, binders, disintegrating agents and the like, may be used. Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, to aid solubility or for preservative purposes, may be included. Injectable suspensions may also be prepared, in which case appropriate liquid carriers, suspending agents and the like may be employed. The pharmaceutical compositions will generally be in the form of a dosage unit, e.g., tablet, capsule, powder, injection, teaspoonful and the like, from about 0.001 to about 50.0 mg/kg, and preferably from about 0.003 to about 25.0 mg/kg of the active ingredients.

The following experimental examples describe the invention in greater particularity and are intended to be a way of illustrating but not limiting the invention.

EXAMPLE 1

Preparation of the Combined Doses of Tramadol and Codeine

For each of the ratios of individual drugs used in the drug combinations tested (Table I), stock solutions were prepared that corresponded to twice the dose of each drug having a concentration expressed in $mg_{drug(s)}$ per 5 mL of distilled water. For example, in the case of the 1:20 tramadol:codeine ratio, 9.1 mg of tramadol hydrochloride (=8.0 mg of tramadol as the base) and 217.1 mg of codeine phosphate (=160.0 mg of codeine as the free base) were each dissolved in separate 5 mL vials of distilled water to form individual stock solutions. Equal volumes of each of the stock solutions were then combined to prepare the final desired drug combination per 10 mL of distilled water. For example, 5 mL of the tramadol stock solution was combined with 5 mL of the codeine stock solution to yield the 1:20 dose, (i.e., 8 mg tramadol:160 mg codeine) in 10 mL of water. Then 10 mL/kg of the stock solution was injected into the mouse. See, Table I. Each ratio was prepared separately in a similar manner and injected in a volume of 10 mL/kg per mouse.

EXAMPLE 2

Preparation of the Combined Doses of Tramadol and Oxycodone

The preparation of different ratios of a tramadol/oxycodone combination is effected by preparing a stock solution having a concentration expressed in $mg_{drugs}$ per 10 mL of dissolved water. For example, 80 mg of tramadol as the free base and 4 mg of oxycodone as the free base are dissolved in 10 mL of water to yield the stock solution of (80 mg:4 mg) tramadol/oxycodone combination per 10 mL of water. The stock solution of the drug combination is then diluted with a sufficient amount of distilled water to prepare the lower doses of the drug combination per 10 mL of dissolved water. For example, 5 mL of the stock 20:1 tramadol/oxycodone combination are diluted with an equal volume of distilled water to yield the lower 20:1 dose, i.e., (40 mg:2 mg), combination per 10 mL of water. Each ratio was prepared separately in a similar manner and injected in a volume of 10 mL/kg per mouse.

EXAMPLE 3

Preparation of the Combined Doses of Tramadol and Hydrocodone

The preparation of different ratios of a tramadol/hydrocodone combination is effected by preparing a stock solution having a concentration expressed in $mg_{drugs}$ per 10 mL of dissolved water. For example, 160 mg of tramadol as the free base and 160 mg of hydrocodone as the free base are dissolved in 10 mL of water to yield the stock solution of (160 mg:160 mg) tramadol/hydrocodone combination per 10 mL of water. The stock solution of the drug combination is then diluted with a sufficient amount of distilled water to prepare the lower doses of the drug combination per 10 mL of dissolved water. For example, 5 mL of the stock 1:1 tramadol/hydrocodone combination are diluted with an equal volume of distilled water to yield the lower 1:1 dose, (i.e., 80 mg:80 mg) combination per 10 mL of water.

EXAMPLE 4

Tramadol N-oxide: Its Synthesis and the Preparation of Doses of Tramadol N-oxide with an Opioid First, tramadol N-oxide was prepared as set forth hereinafter. Tramadol hydrochloride (0.5 mol) was converted its free base in basified water (pH >9) and then extracted with ether. The ether was evaporated to yield the crystalline hydrate of tramadol. The solid was then heated with steam under a high vacuum to remove as much water as possible to yield 131.5 g of material. The material was dissolved in methanol (500 mL) and 65 g of 30% $H_2O_2$ was added. The solution was stirred for 3 hours and then an additional 65 g of the 30% $H_2O_2$ was added. The reaction was then stirred for 2.5 days at room temperature. Approximately 10 mg of $PtO_2$ (use of Pt/C is suggested for its ease of removal) on carbon was then added to the reaction mixture, and very gentle foaming took place. An additional 10 mg of $PtO_2$ was added and the reaction mixture was stirred overnight and then filtered through filter aid. The filtrate was concentrated under vacuum while being heated to a temperature <40° C. The residue was taken up in methylene chloride. Since the methylene chloride solution contained some colloidial platinum, the solution was diluted with ethyl acetate to 1 L and filtered through a nylon filter membrane (0.45 µ pore size) to yield a clear colorless filtrate. The filtrate was concentrated to 600 mL, and then ethyl acetate was added continuously to maintain a volume of 800 mL while the solution was heated until a vapor temperature of 74° C. was reached. The solution was then cooled to room temperature. The solid was collected by filtration, washed with ethyl acetate and dried in vacuo to yield 126.6 g of the tramadol N-oxide (mp. 159.5°–160° C.).

$C_{16}H_{25}NO_3$ Theor.: C, 68.78; H, 9.27; N, 5.01 Found: C, 68.65; H, 9.22; N, 4.99

The preparation of different ratios of a tramadol N-oxide/opioid combination is effected by preparing a stock solution that corresponds to the highest dose of a particular ratio of the tramadol N-oxide/opioid combination having a concentration expressed in $mg_{drugs}$ per 10 mL of distilled water. For example, 160 mg of tramadol N-oxide as the free base and 160 mg of the opiate oxycodone as the free base are dissolved in 10 mL of distilled water to yield the highest dose of the 1:1 (160 mg:160 mg) tramadol N-oxide/oxycodone combination per 10 mL of water. The stock solution of the drug combination is then diluted with a sufficient amount of distilled water to prepare the lower doses of the drug combination per 10 mL of dissolved water. For example, 5 mL of the stock 1:1 tramadol N-oxide/oxycodone combination are diluted with an equal volume of distilled water to yield the lower 1:1 dose (i.e., 80 mg:80 mg) combination per 10 mL of water. Each ratio was prepared separately in a similar manner and injected in a volume of 10 mL/kg per mouse.

EXAMPLE 5

(−) and (+) Enantiomers of O-Desmethyl Tramadol: Their Syntheses and the Preparation of Doses of O-Desmethyl Tramadol with an Opioid First, O-desmethyl tramadol was prepared as set forth hereinafter. Diethylene glycol (125 mL) was added with cooling to potassium hydride (9.5 g) with the temperature being maintained at <50° C. To the solution was added thiophenol (10 mL) dissolved in diethylene glycol (25 mL), and then (−)-tramadol as the free base (9.3 g) in diethylene glycol (50 mL) was added. The final reaction mixture was heated slowly to reflux for 45 minutes. The mixture was cooled and quenched with water. The pH was adjusted to about 3, and the mixture was extracted with ethyl ether. The pH was readjusted to about 8 and the resulting mixture was extracted 5 more times with methylene chloride. The extract was dried and the methylene chloride was evaporated to yield 4.6 g of the title compound. The title compound (4.6 g) was distilled (Kugelrohr), was dissolved in tetrahydrofuran and treated with an ethanol/HCl solution to give 2.3 g of the hydrochloride salt. The salt was recrystallized from ethanol/ethyl ether and dried to yield 1.80 g of the salt of the (−) enantiomer of O-desmethylated tramadol (mp. 242°–3° C.), $[\alpha]_D^{25}$=−32.9 (C=1, EtOH).

$C_{15}H_{23}NO_2$.HCl Theor.: C, 63.04; H, 8.46; N, 4.90 Found: C, 63.00; H, 8.51; N, 4.94

To prepare the (+) enantiomer of the title compound, the reaction was run under the same conditions except that (+)-tramadol as the free base was used instead of the (−)-tramadol to yield 2.8 g of the (+) enantiomer of O-desmethyl tramadol (mp. 242°–3° C.) $[\alpha]_D^{25}$=+32.2 (C=1, EtOH).

$C_{15}H_{23}NO_2$.HCl Theor.: C, 63.04; H, 8.46; N, 4.90 Found: C, 63.14; H, 8.49; N, 4.86

The preparation of different ratios of O-desmethyl tramadol/opioid combinations is effected by preparing a stock solution that corresponds to the highest dose of a particular ratio of the O-desmethyl tramadol/opioid combination having a concentration expressed in $mg_{drugs}$ per 10 mL of distilled water. For example, 160 mg of O-desmethyl tramadol as the free base and 80 mg of the opiate hydrocodone as the free base are dissolved in 10 mL of distilled water to yield the highest dose of a 2:1 (160 mg:80 mg) O-desmethyl tramadol/hydrocodone combination per 10 mL of water. The stock solution of the drug combination is then diluted with a sufficient amount of distilled water to prepare the lower doses of the drug combination per 10 mL of distilled water. For example, 5 mL of the stock 2:1 tramadol O-desmethyl/hydrocodone combination are diluted with an equal volume of distilled water to yield a lower 2:1 dose (i.e., 80 mg:40 mg) combination per 10 mL of water. Each ratio was prepared separately in a similar manner and injected in a volume of 10 mL/kg per mouse.

EXAMPLE 6

Analgesic Activity

Male CD1 mice (weighing from 18–24 g) were utilized in determining the analgesic effects associated with the compositions of the invention. Some mice were dosed orally with the compositions as made in Example 1 and as shown in Table 1 and other mice were dosed orally with the compositions as made in Example 2 and as shown in Table II. The dosing volume was 10 mL/kg.

Analgesic activity was assessed employing the tail-flick test as described by F. D'Amour et al., *J. Pharmacol. Exp. Ther.*, 72, 74 (1941). The test involved subjecting the tail of a mouse to a focused heat stimulus and monitoring the response, i.e., "flicking" (removing) of the tail from the source of the stimulus. The reaction time (latency) of the response was first measured without the administration of any drug composition, and repeated fifteen minutes after the administration of compositions of the invention wherein the components of the compositions are in various ratios. Each mouse was only subjected to one pre- and post-administration test.

The analysis of possible superadditivity for the compositions at each fixed ratio was determined as disclosed by R. J. Tallarida et al., *Life Sci.*, 45, 947 (1989). This procedure involved determination of the total amount in the mixture that is required to produce a specified level of effect, such as 50% ($ED50_{mix}$), and the corresponding total amount that would be expected under simple additivity ($ED50_{add}$). Where it was established that $ED50_{mix} < ED50_{add}$ for a specific fixed-ratio, then that composition ratio is superadditive. Both the lquantities $ED50_{mix}$ and $ED50_{add}$ were random variables; $ED50_{mix}$ was estimated from the dose-response curve for a specific fixed-ratio; $ED50_{add}$ was obtained by combining the ED50 estimates for the two drugs under additivity. $ED50_{mix}$ was then compared to $ED50_{add}$ via a t-test. The ED50 value (95% confidence interval) for tramadol hydrochloride alone was 76.8 (59.2–99.7) mg/kg. The ED50 value (and 95% confidence interval) for codeine phosphate alone was 71.3 (52.0–97.7) mg/kg, and for oxycodone the ED50 was 4.2 (3.0–5.8).

The interaction between tramadol and codeine or hydrocodone were determined at precise dosage ratios of tramadol hydrochloride and codeine or oxycodone. Multiple (typically 4–6) coded doses of each selected combination were studied for analgesic effectiveness after 15 minutes using an experimental design which permitted the complete randomization of the separate dosage forms tested.

Figure 2:
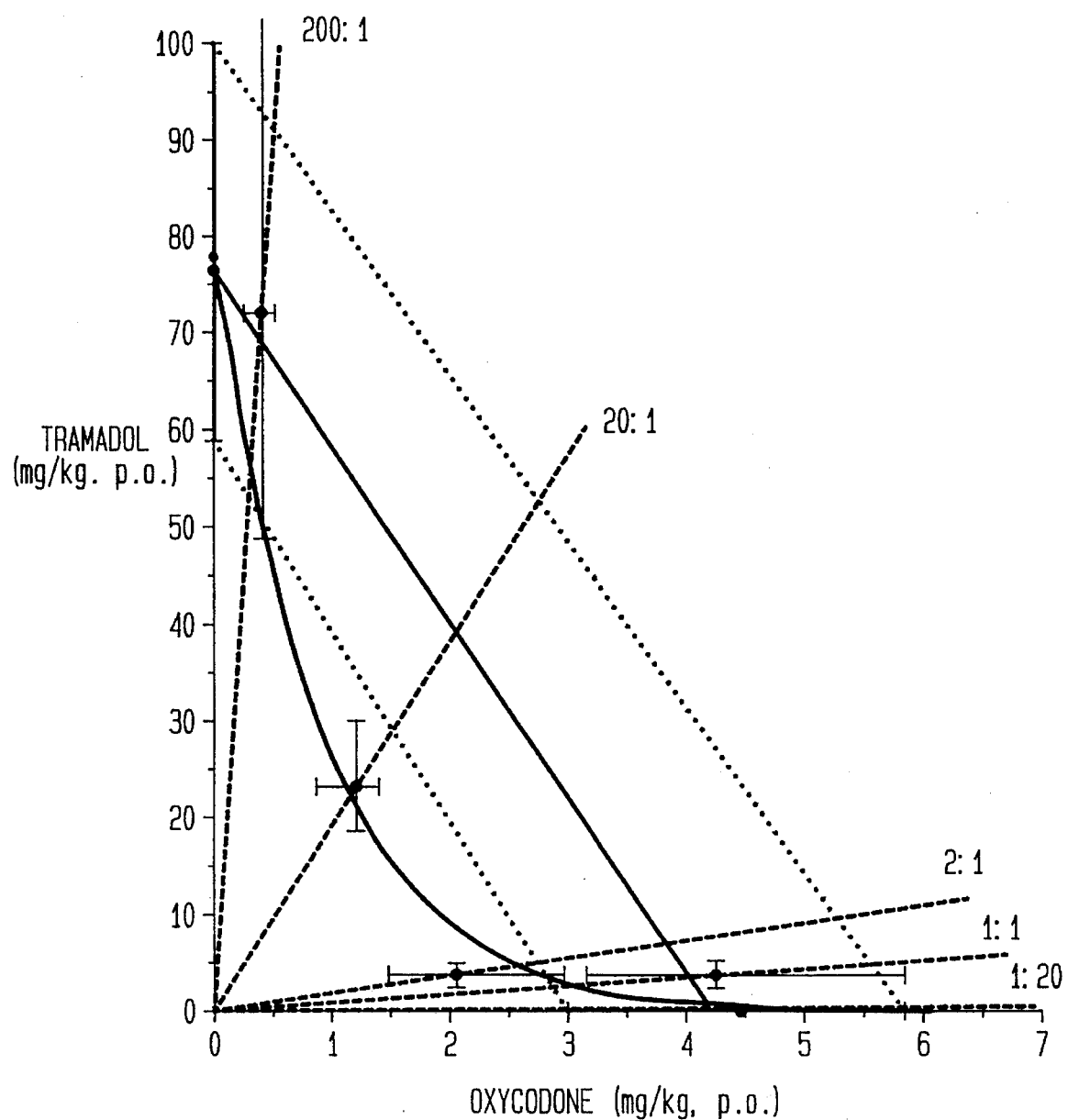
FIG. 2 is an isobologram showing the analgesic effect of tramadol hydrochloride and oxycodone hydrochloride composition on tail-flick latency in mice.

The interaction of tramadol hydrochloride and codeine phosphate or oxycodone sulfate on tail-flick latency in mice was demonstrated by the data in Tables I and II respectively and is shown in FIGS. I and II, Loewe isobolograms, respectively (see, S. Loewe, *Pharm. Rev.*, 9; 237 (1957) regarding the preparation and basis of an isobologram). In the Figures, the diagonal line joining the ED50 values of the two drugs given separately represents the simple additivity of a composition effects at different component ratio. The dotted adjacent lines to the diagonal line define the 95% confidence interval. ED50's falling under the curve (between the line and the origin) indicate superadditivity, i.e., unexpected enhancement of effects. The diagonal dashed lines radiating from the origin represent the dose ratios of tramadol hydrochloride to codeine phosphate (FIG. 1) or oxycodone sulfate (FIG. 2) used in mice receiving the combined drug dosages. The bars through the ED50 points for tramadol and codeine or oxycodone compositions represent the 95% confidence intervals of the ED50.

The experimental data as represented in FIG. I establishes that compositions having a ratio of tramadol to codeine from 1:20 to 20:1 (represented by the curved line) give unexpectedly enhanced activity since $ED50_{mix}$ is less than $ED50_{add}$. The experimental data as represented in FIG. II similarly establishes that compositions having a ratio of tramadol to oxycodone from 200:1 to 1:1 also give unexpectedly enhanced activity. Furthermore, the use of hydrocodone in a composition of the invention is expected to yield a composition with activity similar to a composition comprising oxycodone due to the similar activity profiles and chemical structures of hydrocodone to oxycodone.

TABLE I

| DRUG COMBINATION (Tramadol:Codeine) | TRAMADOL:CODEINE DOSE (mg/kg, p.o.) | | | $ED_{50}$ at 15 min (95% CI's) | |
|---|---|---|---|---|---|
| | Tramadol | Codeine | Analgesia | Tramadol | Codeine |
| tramadol only | 20 | 0 | 0/10 | | |
| | 40 | 0 | 1/10 | | |
| | 80 | 0 | 4/10 | 76.8 | — |
| | 160 | 0 | 9/10 | (59.2–99.7) | |
| | 200 | 0 | 10/10 | | |
| 20:1 | 20 | 1 | 0/10 | | |
| | 40 | 2 | 3/10 | 52.8 | 2.6 |
| | 80 | 4 | 8/10 | (41.5–67.2) | (2.1–3.4) |
| | 160 | 8 | 10/10 | | |
| 2:1 | 10 | 5 | 0/10 | | |
| | 20 | 10 | 3/10 | 30.3 | 15.1 |
| | 40 | 20 | 8/10 | (23.8–38.5 | 11.9–19.3) |
| | 80 | 40 | 10/10 | | |
| 1:1 | 2.5 | 2.5 | 0/10 | | |
| | 5 | 5 | 1/10 | | |
| | 10 | 10 | 4/10 | | |
| | 20 | 20 | 7/10 | 15.4 | 15.4 |
| | 40 | 40 | 7/10 | (10.7–22.2) | (10.7–22.2) |
| | 80 | 80 | 10/10 | | |
| 1:2 | 1 | 20 | 2/10 | | |
| | 2 | 40 | 4/10 | 2.5 | 49.3 |

TABLE I-continued

| DRUG COMBINATION | TRAMADOL:CODEINE | | | | |
|---|---|---|---|---|---|
| | DOSE (mg/kg, p.o.) | | | ED$_{50}$ at 15 min (95% Cl's) | |
| (Tramadol:Codeine) | Tramadol | Codeine | Analgesia | Tramadol | Codeine |
| | 4 | 80 | 6/10 | (1.7–3.6) | (33.3–72.9) |
| | 8 | 160 | 9/9 | | |
| Codeine only | 0 | 10 | 0/10 | | |
| | 0 | 20 | 1/10 | | |
| | 0 | 40 | 1/10 | — | 71.3 |
| | 0 | 80 | 5/10 | | (52.0–97.7) |
| | 0 | 160 | 10/10 | | |

TABLE II

| DRUG COMBINATION | TRAMADOL:OXYCODONE | | | | |
|---|---|---|---|---|---|
| | DOSE (mg/kg, p.o.) | | | ED$_{50}$ at 15 min (95% Cl's) | |
| (Tramadol:Codeine) | Tramadol | Codeine | Analgesia | Tramadol | Oxycodone |
| tramadol only | 20 | 0 | 0/10 | | |
| | 40 | 0 | 2/10 | | |
| | 80 | 0 | 4/10 | 76.8 | — |
| | 160 | 0 | 9/10 | (59.2–99.7) | |
| | 200 | 0 | 10/10 | | |
| 200:1 | 20 | 0.1 | 1/10 | | |
| | 40 | 0.2 | 3/10 | 72.3 | 0.4 |
| | 80 | 0.4 | 3/10 | (49.5–105.6) | (0.2–0.5) |
| | 160 | 0.8 | 10/10 | | |
| 20:1 | 5 | 0.25 | 0/10 | | |
| | 10 | 0.5 | 2/20 | 23.8 | 1.2 |
| | 15 | 0.75 | 3/20 | (18.5–30.6) | (0.9–1.5) |
| | 20 | 1 | 7/10 | | |
| | 40 | 2 | 8/10 | | |
| | 80 | 4 | 9/10 | | |
| 2:1 | 0.625 | 0.3125 | 0/10 | | |
| | 1.25 | 0.625 | 2/10 | | |
| | 2.5 | 1.25 | 3/10 | | |
| | 5 | 2.5 | 6/10 | 4.0 | 2.0 |
| | 10 | 5 | 8/10 | (2.7–6.0) | (1.4–3.0) |
| | 20 | 10 | 9/10 | | |
| | 40 | 20 | 10/10 | | |
| 1:1 | 1.25 | 1.25 | 0/10 | | |
| | 2.5 | 2.5 | 2/10 | | |
| | 5 | 5 | 7/10 | 4.2 | 4.2 |
| | 10 | 10 | 10/10 | (3.1–5.8) | (3.1–5.8) |
| | 20 | 20 | 9/10 | | |
| 1:20 | 0.5 | 10 | 10/10 | | |
| | 0.25 | 5 | 5/10 | 0.2 | 4.4 |
| | 0.125 | 2.5 | 2/10 | (0.2–0.3) | (3.3–5.9) |
| oxycodone only | 0 | 0.5 | 0/10 | | |
| | 0 | 1 | 2/20 | | |
| | 0 | 2 | 3/10 | — | 4.2 |
| | 0 | 3 | 2/10 | | (3.0–5.8) |
| | 0 | 6 | 5/10 | | |
| | 0 | 10 | 9/10 | | |
| | 0 | 20 | 10/10 | | |
| | 0 | 30 | 10/10 | | |

We claim:

1. A pharmaceutical composition comprising a tramadol material selected from the group consisting of tramadol, its stereoisomers and its pharmaceutically acceptable salts and an opioid selected from the group consisting of codeine and oxycodone, wherein the weight ratio of the tramadol material to the opioid is of from about 1:20 to about 20:1.

2. The pharmaceutical composition of claim 1 wherein the opioid is codeine.

3. The pharmaceutical composition of claim 2 wherein the tramadol material is tramadol hydrochloride.

4. The pharmaceutical composition of claim 3 wherein the tramadol hydrochloride is racemic.

5. The pharmaceutical composition of claim 1 wherein the weight ratio is from about 1:2 to about 2:1.

6. The pharmaceutical composition of claim 5 wherein the weight ratio is from about 1:1 to about 2:1.

7. The pharmaceutical composition of claim 1 wherein the opioid is oxycodone.

8. The pharmaceutical composition of claim 7 wherein said tramadol material is tramadol hydrochloride.

9. The pharmaceutical composition of claim 8 wherein the tramadol hydrochloride is racemic.

10. The pharmaceutical composition of claim 9 wherein the weight ratio is from about 20:1 to about 1:1.

11. The pharmaceutical composition of claim 1 further comprising a pharmaceutically acceptable carrier.

12. A method for treating pain in a mammal comprising administering to the mammal an effective amount of the pharmaceutical composition of claim 1.

\* \* \* \* \*